(12) United States Patent
Spivey et al.

(10) Patent No.: US 11,547,783 B2
(45) Date of Patent: Jan. 10, 2023

(54) BLOOD FILTER

(71) Applicants: IMPERIAL COLLEGE INNOVATIONS LIMITED, London (GB); UCL BUSINESS LTD, London (GB)

(72) Inventors: Alan Christopher Spivey, London (GB); Gregory John Quinlan, London (GB); Nathan Davies, London (GB)

(73) Assignees: IMPERIAL COLLEGE INNOVATIONS LIMITED, London (GB); UCL BUSINESS LTD, London (GB)

(*) Notice: Subject to any disclaimer, the term of this patent is extended or adjusted under 35 U.S.C. 154(b) by 0 days.

(21) Appl. No.: 15/532,582

(22) PCT Filed: Dec. 2, 2015

(86) PCT No.: PCT/GB2015/053685
§ 371 (c)(1),
(2) Date: Jun. 2, 2017

(87) PCT Pub. No.: WO2016/087853
PCT Pub. Date: Jun. 9, 2016

(65) Prior Publication Data
US 2018/0015211 A1    Jan. 18, 2018

(30) Foreign Application Priority Data
Dec. 2, 2014   (GB) ...................................... 1421403

(51) Int. Cl.
*A61M 1/02*    (2006.01)
*A61M 1/36*    (2006.01)
(Continued)

(52) U.S. Cl.
CPC ........ *A61M 1/0218* (2014.02); *A61M 1/0259* (2013.01); *A61M 1/3486* (2014.02);
(Continued)

(58) Field of Classification Search
CPC .............. A61M 1/0218; A61M 1/0259; A61M 1/3486; A61M 1/362; A61M 1/3633;
(Continued)

(56) References Cited

U.S. PATENT DOCUMENTS 4,576,928 A * 3/1986 Tani .................... A61M 1/3679
502/400
2012/0294826 A1* 11/2012 Spitalnik .............. A01N 1/0263
424/78.37
(Continued)

FOREIGN PATENT DOCUMENTS

JP    H05131028 A    5/1993
WO    2014176573    10/2014

OTHER PUBLICATIONS

Uzun et al., "Bilirubin removal performance of immobilized albumin in a magnetically stabilized fluidized bed," Journal of Biomaterials Science, Polymer Edition, 2006, vol. 17, No. 7, pp. 791-806.
(Continued)

*Primary Examiner* — Patrick Orme
*Assistant Examiner* — Donovan Bui-Huynh
(74) *Attorney, Agent, or Firm* — Stinson LLP

(57) ABSTRACT

A blood filter device having an iron-chelating molecule, a haem-binding molecule and a haemoglobin-binding molecule bound to a support. Use of the device in a vessel containing blood, for example a blood bag or a flow line, removes haemolysis-derived components from the blood.

19 Claims, 5 Drawing Sheets

Figure 1:
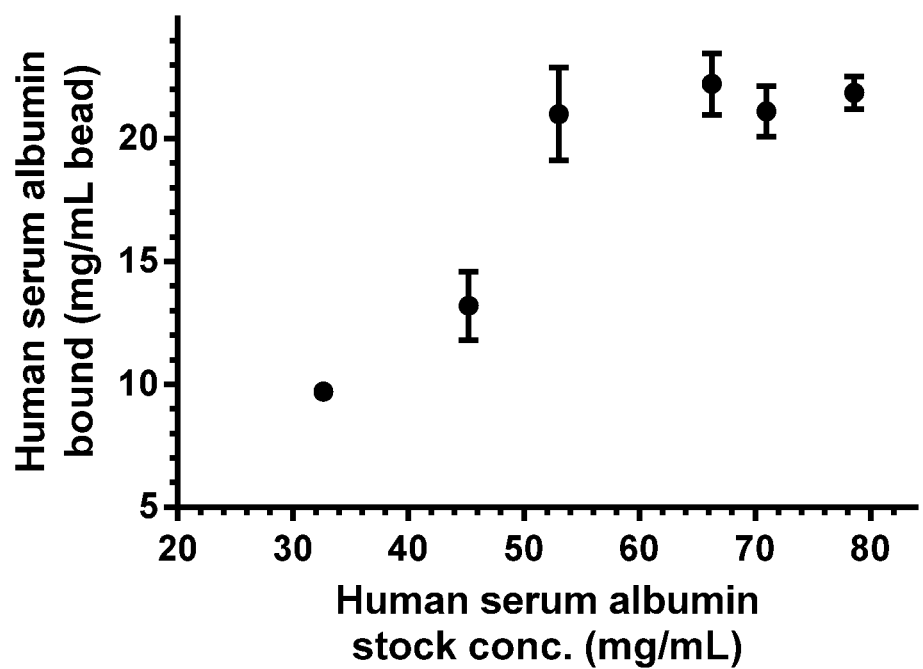

(51) Int. Cl.
*A61M 1/38* (2006.01)
*A61M 1/34* (2006.01)
*A61M 1/00* (2006.01)

(52) U.S. Cl.
CPC .......... *A61M 1/362* (2014.02); *A61M 1/3633* (2013.01); *A61M 1/3679* (2013.01); *A61M 1/3687* (2013.01); *A61M 1/38* (2013.01); *A61M 1/88* (2021.05)

(58) Field of Classification Search
CPC .... A61M 1/3679; A61M 1/3687; A61M 1/38; A61M 1/0094; A61M 2202/0415; A61M 2230/005; A61M 2202/0057; A61M 2202/0413; A61M 2202/046; A61M 2202/0433; A61M 1/34; A61M 1/88; A61M 1/3472; A61K 31/16; A61K 2035/124; A61K 31/4196; A61K 31/4412; A61K 31/4439; A61K 31/444; A61K 31/55; A61K 31/555; A61K 35/14; A61K 35/18; A61K 38/40; A61K 47/61; A61K 47/62; A61K 38/1709; A61K 45/06; A61K 47/42; A61K 38/42; B01J 20/3204; B01J 20/3212; B01J 20/3219; B01J 20/327; B01J 20/3274; B01J 20/267; B01J 20/28016; B01J 20/28073; B01J 20/28076; B01J 20/2808; B01J 20/28083; B01J 20/28085; B01J 20/3261; A01N 1/021; A01N 1/0263; A61J 1/05; A61J 1/10; A61P 7/00; A61P 7/08; B01D 15/00; B01D 15/36; B01D 2239/0485; B01D 2239/1241; B01D 2239/125; B01D 39/06; B01D 39/2013; B01D 39/2031; B01D 39/2037; B01D 67/0088; B01D 67/0093; B01D 20/3212; B01D 20/3219; B01D 20/327; B01D 20/267; B01D 20/28016; B01D 20/28073; B01D 20/28076; B01D 20/2808; B01D 20/28083; B01D 20/28085; B01D 20/3261; C08F 236/20; C12N 5/0641; G01N 21/79; Y10S 514/832; Y10S 514/833; Y10S 514/836; Y10S 514/97; C07K 14/47; C07K 14/4717; C07K 14/805; Y02A 50/30

See application file for complete search history.

(56) References Cited

U.S. PATENT DOCUMENTS

2015/0118673 A1\* 4/2015 Chan ...................... A01N 1/021
435/1.1
2016/0089399 A1\* 3/2016 Perlstein ................ G01N 21/79
435/2

OTHER PUBLICATIONS

International Search Report, PCT/GB2015/053685, dated Feb. 26, 2016, 4 pages.
Written Opinion, PCT/GB2015/053685, dated Feb. 26, 2016, 6 pages.
Horak, D., et al., "Magnetic Poly(2-hydroxyethyl methacrylate) Microspheres for Affinity Purification of Monospecific Anti-p46 kDa/Myo1C Antibodies for Early Diagnosis of Multiple Sclerosis Patients," 2017, Bioscience Reports, 37:10 pages.
Horak, D., et al., "Poly(2-hydroxyethyl methacrylate) Emboli with Increased Haemostatic Effect for Correction of Haemorrhage of Complex Origin in Endovascular Surgery of Children," 2008, J Mater Sci: Mater Med, 19:1265-1274, 10 pages.

\* cited by examiner

A

B

BLOOD FILTER

REFERENCED TO RELATED APPLICATIONS

This application is a U.S. national stage application of International Patent Application No. PCT/GB2015/053685, filed Dec. 2, 2015, and claims the benefit of priority of Great Britain Application No. 1421403.5, filed Dec. 2, 2014, the entire disclosures of which are incorporated herein by reference.

The present invention relates to the removal of haemolysis-derived components from blood and, in particular, to a device for achieving this.

BACKGROUND

Approximately 85 million blood transfusions are administered globally per year. In the US, the maximum storage period for blood and blood products is 42 days. In the UK, the maximum storage period for red blood cells (RBCs, or erythrocytes) and whole blood is 35 days, with additional EU regulations requiring that the level of haemolysis be <0.8%, and that >75% of the transfused RBCs survive in the circulation 24 hours post-administration. Prolonging the viable lifespan of stored blood products would reduce costs and demand for new samples and reduce the wastage caused by having to dispose of blood products that have gone beyond the permitted storage period. Measures to improve the lifespan of stored blood would also improve the quality of stored blood during the current storage periods.

A number of approaches have been introduced to improve the quality of stored blood and potentially extend its maximum storage period. These include the development of sterile yet breathable plastics and polymers to allow gas exchange and the fractionation and extraction of certain undesirable blood components (e.g. platelets to prevent clotting).

Transfusion of stored blood and the process of blood extraction for storage or during extracorporeal procedures expose blood to significant stresses, for example mechanical stress and sheering forces, as well as osmotic and thermal stress. These stresses can increase haemolysis and red blood cell fragility, which are contributory factors in the short shelf-life of stored blood and can lead to haemolysis-associated pathologies in blood recipients.

The present invention addresses the problem of improving the quality of stored blood, prolonging the lifespan of stored blood, as well as reducing the adverse effects caused by the stresses associated with blood transfusion and extracorporeal circulation. A device of this nature will allow for extended storage periods for blood products and maximal benefit of this important limited resource, as well as improved patient benefit and safety for recipients of transfusions of stored blood or blood from extracorporeal circuits.

WO2014/176573 describes a filter formed of a styrene-divinylbenzene co-polymer (Chelex®) resin. The filter is described to bind free iron ions in solution. No evidence of the filter binding to haem or haemoglobin is provided, nor is any reduction in haemolysis demonstrated.

SUMMARY OF INVENTION

Haemolysis is the rupture (lysis) of red blood cells (RBCs, or erythrocytes) leading to the release of the cellular contents. As a result of haemolysis, free haemoglobin, haem and iron are released into the blood circulation. Although endogenous protection mechanisms are available, if they are overwhelmed then these haemolysis-derived components can initiate organ injury, and pro-inflammatory responses. Increased haemolysis can also lead to altered extracellular iron status, resulting in iron-catalysed oxidative damage and organ dysfunction associated with critical illness and mortality. At risk populations include those suffering from haemolytic anaemia, for example as a result of infection (e.g. malaria, yellow fever, dengue fever), hereditary haeomglobinopathies (e.g. sickle cell disease, thalassemia) or otherwise acquired (e.g. drug-induced haemolytic anaemia, HELLP syndrome). Other haemolysis-associated conditions include haemorrhagic conditions.

Those receiving blood transfusions are also at risk from the effects of these haemolysis-derived components. Blood for transfusion has the potential to introduce the products of haemolysis into the circulation as the age of stored blood, storage conditions, routine manipulation of blood bags, irradiation of blood for use in individuals given stem cell transplants to reduce host versus graft disease, washing of fresh blood and donor variability all contribute to haemolysis in this setting. Moreover, extensive literature exists demonstrating associations between the length of blood storage, levels of haemolysis in transfused blood, and adverse outcomes post-transfusion including transfusion related acute lung injury (TRALI), acute kidney injury and pulmonary hypertension (Wang, D. et al. (2012) Transfusion of older stored blood and risk of death: a meta-analysis. *Transfusion* 52, 1184-95; Schaer, D. J. and Buehler, P. W. (2013) Cell-free hemoglobin and its scavenger proteins: new disease models leading the way to targeted therapies. Cold Spring Harb. Perspect. Med. 3; Tung, J.-P. et al. (2012) Age of blood and recipient factors determine the severity of transfusion-related acute lung injury (TRALI). Crit. Care 16, R19; Zimrin, A. B. and Hess, J. R. (2009) Current issues relating to the transfusion of stored red blood cells. Vox Sang. 96,93-103, the contents of which are incorporated by reference in their entirety). Although haemolysis is unlikely to be the only component that is involved in these adverse responses, it may be a contributory factor. Additionally, the generation of damaging reactive oxygen species (ROS) instigated by free haemoglobin, iron and haem are mechanistically the predominant cause for recipient tissue damage seen under these circumstances. Adverse responses linked to microbial virulence may also be important given that the iron-containing products of haemolysis are microbial virulence factors.

Generation of these haemolysis-derived components is not just limited to responses within the recipient following administration of the stored blood. Ongoing accumulative damage to packed cells occurs once haemolysis begins, and consequent lipid peroxidation and protein oxidation within the stored blood not only propagates further haemolysis of these cells (autocatalysis), but also contributes to red cell fragility increasing the likelihood of rupture and additional haemolysis on transfusion. Additionally, products of ROS damage, such as aldehydes formed as end products of lipid peroxidation, are bioactive and even toxic in high enough doses and thus can further contribute to pro-inflammatory responses at and post-transfusion.

Whilst natural protection against the effects of haemolysis is afforded by endogenous mechanisms, these systems are rapidly overwhelmed. In light of these circumstances, there is a clear need to reduce the levels of these haemolysis-derived components both in stored blood, transfused blood, and in a patient's circulation.

Figure 4:
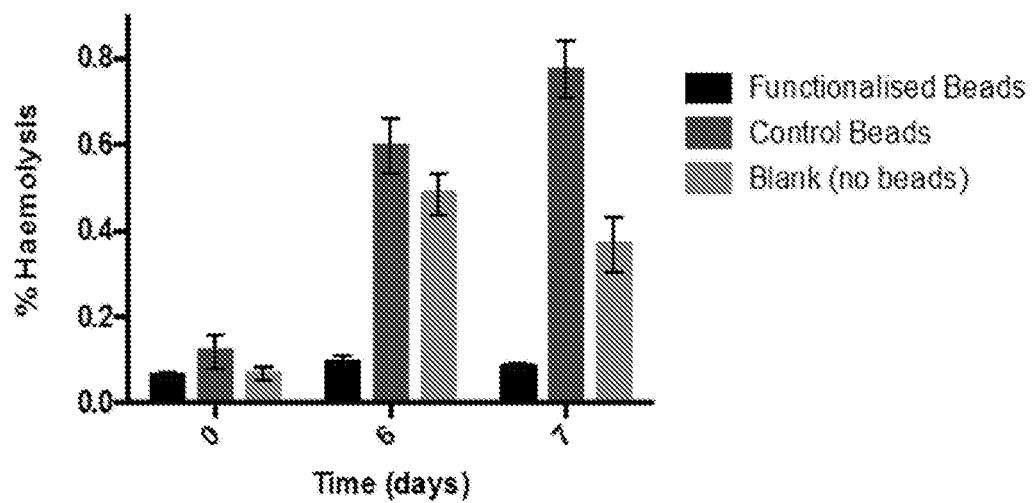
Figure 4:
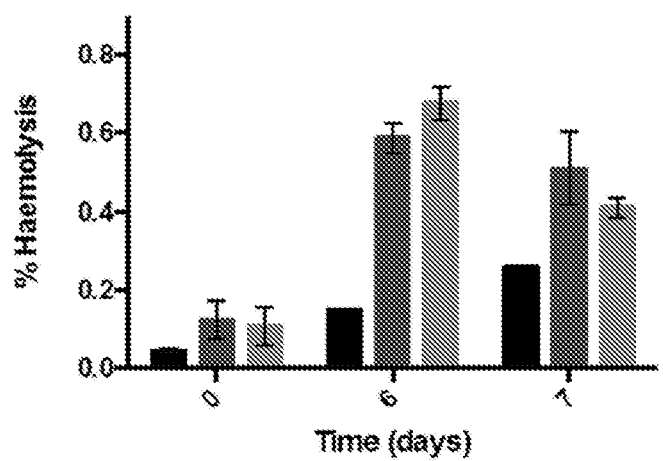

Achieving a reduction of haemolysis and haemolysis-derived products is not straightforward—for example, extracorporeal filtration devices are known to cause haemolysis. As demonstrated herein (Example 2), exposure of blood products to some filter substrates or structures can in fact increase haemolysis (FIG. 4). Therefore, a filter intended to remove a haemolysis product may in fact worsen haemolysis, and also thereby increase the amount of haemolysis-derived components in blood products. Surprisingly, therefore, it is identified in the present application that by using a device having a combination of a haemoglobin-binding molecule, a haem-binding molecule and an iron-chelating molecule, haemolysis can be reduced, as can the level of haemolysis-derived components. A decrease in the level of haemolysis-derived components is particularly effective, as reducing the level of haemolysis-derived components limits the impact of these components triggering further autocatalytic haemolysis. Furthermore, the undesirable increase of haemolysis as a result of exposure of RBCs to filter structures is overcome. The invention is particularly advantageous as the combination of binding agents provides a "single-action" filter. Such a "single action" device allows haemoglobin, haem and free iron to be removed in a single step. This provides an advantage greater than the additive effect of using the 3 binding agents separately, as it reduces the risk of haemolysis triggered by exposure to filter substrates being exacerbated during sequential filter steps.

Therefore, in a first aspect the present invention provides a device that will effectively and selectively remove the damaging products of haemolysis (haemoglobin, haem and free iron) from blood. Accordingly, in a first embodiment the invention provides a device for removal of haemolysis-derived components from blood, the device comprising: a support, a plurality of binding agents bound to said support, wherein the binding agents comprise at least one iron-chelating molecule, at least one haemoglobin-binding molecule, and at least one haem-binding molecule. In certain embodiments the device further comprises a vessel for the storage or passage of blood, wherein the vessel contains the support.

In certain embodiments, the support is a plurality of beads. In certain such embodiments each bead of the plurality of beads is bound to no more than one of: the iron-chelating molecule, the haemoglobin-binding molecule, and the haem-binding molecule. In an alternative embodiment, the support is a single element to which at least one iron-chelating molecule, at least one haemoglobin-binding molecule, and at least one haem-binding molecule are bound, preferably wherein all of the plurality of binding agents are bound to the single element.

In certain embodiments wherein the device comprises a vessel containing the support, the support is wholly or partially integrated with the vessel. Alternatively, in certain embodiments the support is not integrated with the vessel.

In certain embodiments the support comprises an insoluble polymer or glass. Suitable insoluble polymers include natural functionalised biopolymers, such as a polysaccharide polymer (e.g. agarose), and synthetic polymers, such as polystyrene-, polyacrylamide-, and polyethylene-based polymers. In certain embodiments, the insoluble polymer is a polysaccharide polymer. In certain such embodiments, the insoluble polymer is agarose. In certain alternative embodiments, the insoluble polymer is a synthetic polymer. In certain such embodiments, the synthetic polymer is a co-polymer/grafted (e.g. PEGylated).

In certain embodiments the iron-chelating molecule is desferrioxamine (DFO). In certain embodiments the haemoglobin-binding molecule is haptoglobin (Hp). In certain embodiments, the haem-binding molecule is serum albumin, preferably human serum albumin (HSA). In certain embodiments, the haemoglobin-binding molecule, the haem-binding molecule, and the iron-chelating molecule are present in the proportions 50-90%, 5-50% and 1-30% respectively.

In certain embodiments the device is for in vitro or ex vivo removal of haemolysis-derived components from blood.

In certain embodiments, the device comprises a support, a plurality of binding agents bound to said support, wherein the binding agents comprise at least one DFO molecule, at least one haptoglobin molecule, and at least one HSA molecule. In certain such embodiments the support is optionally a plurality of agarose beads. In certain such embodiments, the device optionally further comprises a vessel for the storage or passage of blood, wherein the vessel contains the support.

In a second aspect, the present invention relates to an apparatus comprising a device according to the first aspect. In certain embodiments the apparatus is suitable for use as an extracorporeal blood circulation system. In certain embodiments the apparatus is suitable for delivering blood from a blood bag to a patient.

In a third aspect, the invention provides a method for removing haemolysis-derived components from a blood sample, the method comprising applying the blood sample to a device according to the first aspect or to an apparatus according to the second aspect of the invention.

In a fourth aspect the invention provides a method of treating or preventing haemolysis-associated pathology in a subject comprising, applying blood from a subject to a device according to the first aspect or an apparatus according to the second aspect and administering said blood to a subject. In certain embodiments the subject from which the blood is taken and the subject to which the blood is administered is the same subject.

In a fifth aspect the invention provides an iron-chelating molecule for use in the treatment or prevention of haemolysis-associated pathology in a subject, wherein the iron-chelating molecule is bound to a support to which at least one haemoglobin-binding molecule, and at least one haem-binding molecule are also bound.

In a sixth aspect the invention provides a haemoglobin-binding molecule for use in the treatment or prevention of haemolysis-associated pathology in a subject, wherein the haemoglobin-binding molecule is bound to a support to which at least one iron-chelating molecule, and at least one haem-binding molecule are also bound.

In a seventh aspect the invention provides a haem-binding molecule for use in the treatment or prevention of haemolysis-associated pathology in a subject, wherein the haem-binding molecule is bound to a support to which at least one iron-chelating molecule, and at least one haemoglobin-binding molecule are also bound.

In certain embodiments of the fourth, fifth, sixth and seventh aspects of the invention, the haemolysis-associated pathology treated or prevented is selected from hypertension, vaso-occlusion, vascular injury, atherosclerosis, organ injury or failure (e.g. TRALI), acute respiratory distress syndrome, and systemic inflammatory response syndrome. In certain embodiments, the haemolysis-associated pathology treated or prevented is abnormal or aberrant thrombosis. In certain embodiments, the haemolysis-associated pathology treated or prevented is a bacterial infection. Haemolysis-derived components are bacterial virulence factors and, therefore, removing haemolysis-derived components and reducing haemolysis will prevent or treat bacterial infection.

In certain embodiments of the fourth, fifth, sixth and seventh aspects of the invention, the haemolysis associated pathology is caused by haemolytic anaemia, a haemoglobinopathy, autoimmune-induced haemolysis (e.g. Paroxysmal nocturnal haemoglobinuria (PNH)), drug-induced autoimmune haemolysis, drug-induced non-autoimmune haemolysis, infection, HELLP syndrome, haemorrhagic conditions, administration of stored blood, administration of shed blood, or use of a cardiac pump, whether extracorporeal (e.g. as part of dialysis or extracorporeal membrane oxygenation (ECMO)) or in situ (e.g. a ventricular assist device).

The present disclosure will now be described further. In the following passages different aspects/embodiments of the disclosure are defined in more detail. Each aspect/embodiment so defined may be combined with any other aspect/embodiment or aspects/embodiments unless clearly indicated to the contrary. In particular, any feature indicated as being preferred or advantageous may be combined with any other feature or features indicated as being preferred or advantageous.

FIGURES

FIG. 1: Binding capacities of human serum albumin (HSA) to the agarose matrix in PBS. HSA-agarose beads were shown to bind to haem.

Figure 2:
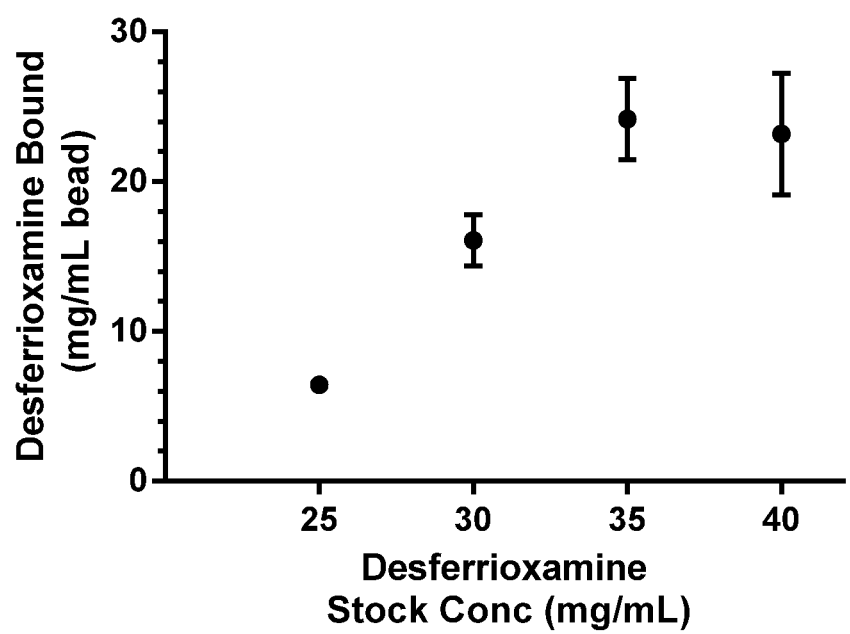

FIG. 2: Binding capacities of desferrioxamine (DFO) to the agarose matrix in PBS. DFO-agarose beads were shown to bind iron ions.

Figure 3:
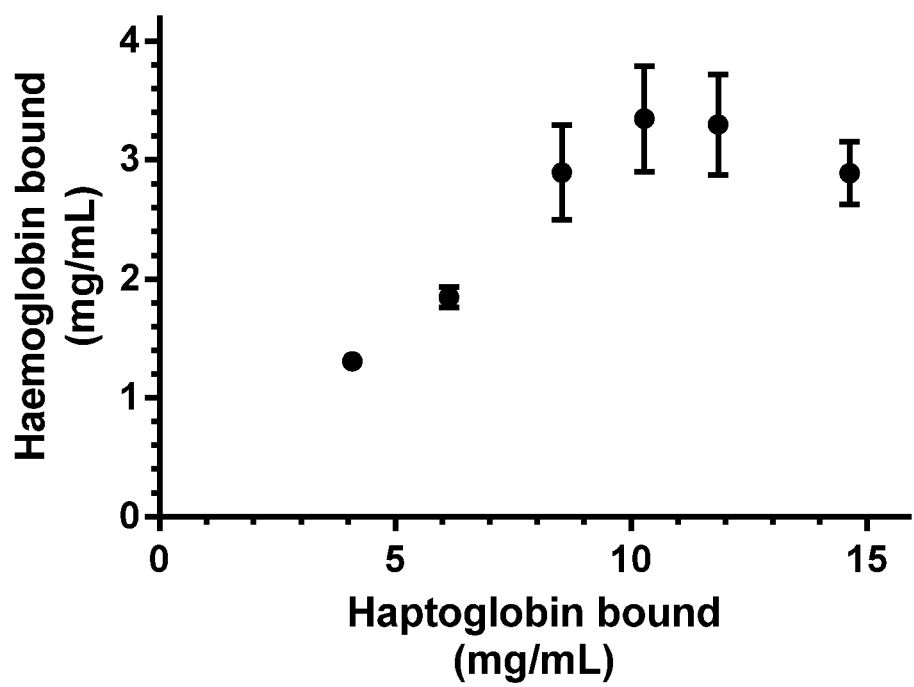

FIG. 3: Binding capacity of haptoglobin-agarose beads for human haemoglobin.

FIG. 4: Time course showing percentage haemolysis of RBCs in citrate-phosphate buffer (A) and AS-3 (B) when exposed to sepharose beads functionalised with Hp, HSA and DFO (left column), control beads (middle column) and no beads (right column). Percentages are presented for days 0, 6 and 7.

Figure 5:
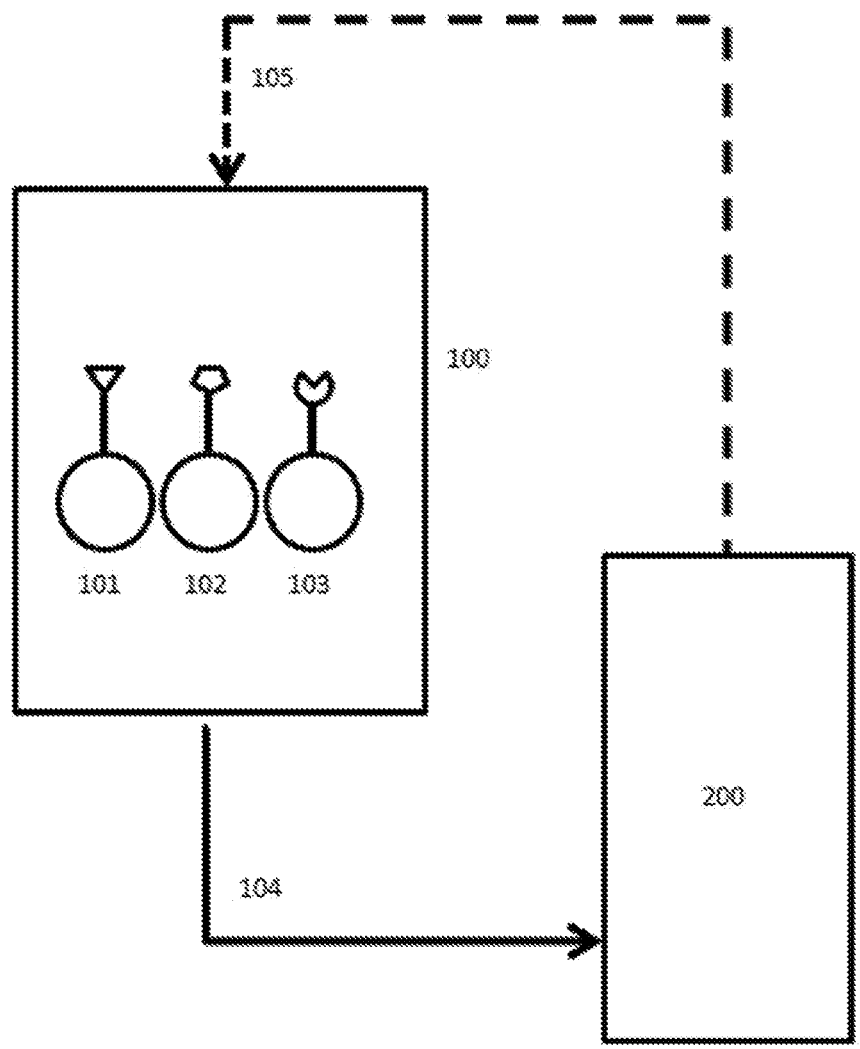

FIG. 5: Schematic diagram showing vessel 100 containing a support comprising a plurality of beads (101-103). Each bead is bound to only one type of binding molecule, either an iron-chelating molecule (101), a haemoglobin-binding molecule (102), or a haem-binding molecule (103). Blood contained in vessel 100 can pass down flowline 104 to patient 200. In certain embodiments, flowline 105 can deliver blood from patient 200 to vessel 100 so as to form an extracorporeal blood circulation apparatus.

DETAILED DESCRIPTION

As used herein, blood is any blood product comprising haemolysis-derived components, in particular blood products comprising erythrocytes. It includes whole blood (i.e. unfractionated blood extracted from a patient), stored blood (e.g. for transfusions), blood taken ex vivo from a patient (e.g. as a blood sample or donation, shed blood (i.e. during surgical procedures) or as part of an extracorporeal blood circulatory system), and blood used in vitro. As will be appreciated by the skilled person, blood products suitable for use with the invention may include anticoagulants and/or buffers. Preferably the blood is from a mammalian subject, more preferably from a human subject.

Haemolysis, or the rupture of red blood cells, leads to the release of free haemoglobin (Hb) into the blood. Free haemoglobin tetramers degrade first to dimers and then release free haem, with the potential to release free iron at any stage. Each of these components (Hb, haem and free iron) is a haemolysis-derived component as used herein. As used herein, haemoglobin (Hb), or free haemoglobin, encompasses Hb in tetrameric form and in dimeric form and at all known oxidation states, including met, oxy and ferryl forms. As used herein, haem, or free haem, includes the different physiological haem molecules, for example haem A, haem B, haem C and haem O, and all oxidation states thereof. As used herein, iron, or free iron, includes $Fe^{2+}$ and $Fe^{3+}$ ions and all other oxidation states.

The present invention provides a device for removing haemolysis-derived components from blood, wherein the device comprises a support, a plurality of binding agents bound to said support and wherein the binding agents comprise at least one iron-chelating molecule, at least one haemoglobin-binding molecule, and at least one haem-binding molecule. The invention also provides an apparatus comprising said device and methods for using said device. The invention further provides methods of treating haemolysis-associated pathologies using the at least one iron-chelating molecule, at least one haemoglobin-binding molecule, and at least one haem-binding molecule bound to a support.

The advantages of the present invention include both reducing the effects of haemolysis when administering blood, as well as reducing haemolysis in stored blood. Haemolysis can be caused by mechanical and osmotic stresses, as well as temperature changes. When blood is transfused into a patient, whether as part of an extracorporeal circulation system or from a stored blood sample, haemolysis occurs due to the mechanical forces to which the blood is exposed, for example when forced at high flow rate through an aperture or when passing through a pump. As already described, haemolysis-derived components can trigger unwanted pro-inflammatory responses in a patient and lead to oxidative damage and organ injury and failure. The use of a device according to the invention can act to filter the haemolysis-derived components from the blood being transfused and thereby limit the harmful effects of haemolytic by-products in a patient undergoing blood transfusion. Without being bound by theory, removal of haemolysis-derived components and reducing haemolysis also has the effect of limiting autocatalytic haemolysis triggered by the presence of haemolysis-derived components.

Furthermore, the removal of haemolysis-derived components and reduction in haemolysis when using the invention is particularly effective as the combination of binding agents provides a "single-action" filter. Such a "single action" device allows haemoglobin, haem and free iron to be removed in a single step, thereby reducing the demonstrated risk of haemolysis triggered by exposure to filter substrates being exacerbated during sequential filter steps.

A number of diseases and conditions can lead to pathological haemolysis in a patient's own circulatory system, for example haemolytic anaemia. Haemolytic infections include malaria, yellow fever, and dengue fever. Haemolysis may also be caused by hereditary conditions, for example haemoglobinopathies such as alpha, beta and delta thalassemia and sickle cell disease. Other causes of the release of haemolysis-derived components include drug-induced autoimmune haemolysis, drug-induced non-immune haemolysis, autoimmune haemolysis, HELLP syndrome, and haemorrhagic conditions. As a result, the patient may suffer haemolysis-associated pathologies such as organ failure, hypertension, acute respiratory distress syndrome, haemochromatosis and immune dysregulation. These symptoms and conditions may be treated or prevented using devices, apparatuses and methods according to the present invention. For example, one or more of the symptoms and conditions may be treated or prevented by using an extracorporeal circulatory system incorporating a device according to the invention. In such a system, blood extracted from the patient is contacted with the device in order to remove the haemolysis-derived components, such that blood reintroduced into the patient contains reduced levels of haemolysis-derived components, thereby reducing the haemolysis-associated pathology.

When blood is stored, for example blood donations to be used in future transfusions, one of the limitations of the shelf-life of such blood samples is the accumulation of haemolysis-derived components which would be harmful if administered to a patient. The use of a device according to the invention during storage also has the advantages of removing the haemolysis-derived components described above—i.e. treating and preventing haemolysis-associated pathologies. For the purposes of blood storage, the invention further provides the additional advantage of reducing the accelerated degradation as a result of autocatalytic haemolysis, as well as reducing iron or haem-catalysed ROS generation during storage, thereby reducing the effects related to red cell fragility. Each of these effects, whether alone or in combination, means the use of the present invention can significantly prolong the shelf-life of stored blood. In certain embodiments the extension in maximal storage lifespan of the stored blood as a result of the present invention is at least 5 days, at least 10 days, at least 15 days, at least 20 days, at least 30 days, at least 50 days.

The device and methods according to the present invention comprise at least one iron-chelating molecule bound to a support. Iron-chelating molecules suitable to be used in accordance with the invention are molecules with high affinity for iron ions. In certain embodiments the at least one iron-chelating molecule is selected from desferrioxamine (DFO) (also known as deferoxamine), diferiprone, defarsirox, transferrin, and lactoferrin. In certain preferred embodiments, the iron-chelating molecule is DFO. In certain embodiments, only one type of iron-chelating molecule is bound to the support. In certain such embodiments, the only one type of iron-chelating molecule bound to the support is DFO. In certain alternative embodiments, more than one type of iron-chelating molecule is bound to the support.

In certain embodiments, the at least one iron-chelating molecule is covalently bound to the support. In certain embodiments the at least one iron-chelating molecule is covalently bound to the support via a spacer moiety. Alternatively, in certain embodiments the at least one iron-chelating molecule is covalently bound directly to the support. Suitable linkers appropriate to any given support-binding-molecule combination would be appreciated by one skilled in the art of solid-support chemistry. In certain embodiments wherein the at least one iron-chelating molecule is DFO, the DFO is bound to the support via an amine, ether, amide, ester, sulfone, or sulphonamide linkage, for example an amine linkage.

The device and methods according to the present invention comprise at least one haemoglobin (Hb)-binding molecule bound to a support. Hb-binding molecules suitable to be used in accordance with the invention are binding agents with high affinity for haemoglobin either as a dimer or tetramer or both. Suitable such binding agents include naturally-occurring or synthetic proteins, glycoproteins, lipoproteins and immunoglobulins, for example antibodies. In certain embodiments the at least one Hb-binding molecule is haptoglobin (Hp). In such embodiments, haptoglobin may be present as the Hp1 isoform, the Hp2 isoform, the Hp2-1 isoform or any combination thereof. In certain alternative embodiments, the Hb-binding molecule is a synthetic peptide.

In certain embodiments, only one type of Hb-binding molecule is bound to the support. In certain such embodiments, the only one type of Hb-binding molecule bound to the support is haptoglobin. In certain such embodiments, the only one type of Hb-binding molecule bound to the support is Hp1. In certain embodiments the only one type of Hb-binding molecule bound to the support is Hp2. In certain embodiments the only one type of Hb-binding molecule bound to the support is Hp2-1. In certain alternative embodiments, more than one type of Hb-binding molecule is bound to the support.

In certain embodiments, the at least one Hb-binding molecule is covalently bound to the support. In certain embodiments the at least one Hb-binding molecule is covalently bound to the support via a spacer moiety. Alternatively, in certain embodiments the at least one Hb-binding molecule is covalently bound directly to the support. In embodiments wherein the at least one Hb-binding molecule is haptoglobin (including one or more isoforms thereof), the haptoglobin is bound to the support via an amine linkage at a lysine amino acid residue. In an alternative embodiment, the haptoglobin is bound to the support with a linkage via a sulphur group of a cysteine residue.

The device and methods according to the present invention comprise at least one haem-binding molecule bound to a support. Haem-binding molecules for use according to the invention are binding agents with high affinity for haem. Haem as used herein encompasses any or all of the different physiological haem molecules, for example haem A, haem B, haem C and haem O, and all oxidation states thereof. Suitable such binding agents include naturally-occurring or synthetic proteins, glycoproteins, lipoproteins and immunoglobulins, for example antibodies. In certain embodiments the at least one haem-binding molecule is serum albumin. In certain such embodiments, the haem-binding molecule is human serum albumin (HSA). In certain alternative embodiments, the haem-binding molecule is hemopexin. In certain embodiments, only one type of haem-binding molecule is bound to the support. In certain such embodiments, the only one type of haem-binding molecule bound to the support is serum albumin. In certain such embodiments, the only one type of haem-binding molecule bound to the support is HSA. In certain alternative embodiments, more than one type of iron-chelating molecule is bound to the support.

In certain embodiments, the at least one haem-binding molecule is covalently bound to the support. In certain embodiments the at least one haem-binding molecule is covalently bound to the support via a spacer moiety. Alternatively, in certain embodiments the at least one haem-binding molecule is covalently bound directly to the support. In embodiments wherein the at least one haem-binding molecule is serum albumin, preferably HSA, the serum albumin is bound to the support via an amine linkage at a lysine amino acid residue. In an alternative embodiment, the HSA is bound to the support with a linkage via a sulphur group of a cysteine residue.

In certain embodiments of the present invention, a greater amount of the Hb-binding molecule is bound to the support than the amount of haem-binding molecule bound to the support, and a greater amount of the haem-binding molecule is bound to the support than the amount of iron-chelating molecule bound to the support. That is, the amount of each binding agent bound to the support follows the following relationship:

Hb-binding molecule>haem-binding molecule>iron-chelating molecule

In certain embodiments of the invention, the percentage of the total Hb-binding molecules, haem-binding molecules and iron-chelating molecules bound to the support which are Hb-binding molecules is at least 50%, at least 60%, at least 65%, at least 70%, at least 80%, at least 85%, at least 90%. In certain embodiments, the proportion of binding molecules bound to the support which are Hb-binding molecules is 50% to 90%, optionally 60%-80%, optionally 65%-80%, optionally 60%-70%. In certain embodiments, the proportion of binding molecules bound to the support which are Hb-binding molecules is 50%, 55%, 60%, 65%, 70%, 75%, 80%, 85%, 90%.

In certain embodiments of the invention, the percentage of the total Hb-binding molecules, haem-binding molecules and iron-chelating molecules bound to the support which are haem-binding molecules is at least 5%, at least 10%, at least 15%, at least 20%, at least 30%, at least 40%, at least 45%, at least 50%. In certain embodiments, the proportion of binding molecules bound to the support which are haem-binding molecules is 5% to 50%, optionally 10%-40%, optionally 10-20%, optionally 15%-30%, optionally 20%-30%. In certain embodiments, the proportion of binding molecules bound to the support which are Hb-binding molecules is 5%, 10%, 15%, 20%, 25%, 30%, 35%, 40%, 45%, 50%. In certain embodiments, the percentage of the total Hb-binding molecules, haem-binding molecules and iron-chelating molecules bound to the support which are haem-binding molecules is at least 0.5%, at least 0.6%, at least 0.7%, at least 0.8%, at least 0.9%, at least 1%, at least 1.1%, at least 1.2%, at least 1.3%, at least 1.4%, at least 1.5%, at least 2%, at least 3%, at least 4%, at least 5%.

In certain embodiments of the invention, the percentage of the total Hb-binding molecules, haem-binding molecules and iron-chelating molecules bound to the support which are iron-chelating molecules is at least 1%, at least 2%, at least 5%, at least 6%, at least 7%, at least 8%, at least 9%, at least 10%, at least 15%, at least 20%, at least 25%, at least 30%. In certain embodiments, the proportion of binding molecules bound to the support which are iron-chelating molecules is 1% to 30%, optionally 1%-20%, optionally 5%-20%, optionally 5%-15%, optionally 5%-10%. In certain embodiments, the proportion of binding molecules bound to the support which are iron-chelating molecules is 1%, 2%, 5%, 10%, 15%, 20%, 25%, 30%.

In certain embodiments, the relative amounts of Hb-binding molecules, haem-binding molecules and iron-chelating molecules bound to the support are 50%-90% Hb-binding molecules, 5%-50% haem-binding molecules and 1%-30% iron-chelating molecules as a percentage of the total Hb-binding molecules, haem-binding molecules and iron-chelating molecules bound to the support. In certain preferred embodiments, the relative amounts are 60%-70% Hb-binding molecules, 10%-20% haem-binding molecules and 5%-15% iron-chelating molecules as a percentage of the total Hb-binding molecules, haem-binding molecules and iron-chelating molecules bound to the support. In certain other preferred embodiments, the relative amounts are 65%-80% Hb-binding molecules, 10%-20% haem-binding molecules and 5%-10% iron-chelating molecules as a percentage of the total Hb-binding molecules, haem-binding molecules and iron-chelating molecules bound to the support.

In certain embodiments, the haemoglobin-binding molecule is bound to the support in an amount such that under maximal binding of all of the plurality of binding agents bound to the support, haemoglobin is at least 85% of the molecular weight of bound haemolysis-derived components. That is, in such embodiments, if all binding agents on the support had their ligand bound, haemoglobin would account for at least 85% of the total molecular weight of the bound ligands. In certain such embodiments, the haemoglobin-binding molecule is bound to the support in an amount such that under maximal binding of all of the plurality of binding agents bound to the support, haemoglobin is optionally at least 90%, at least 95%, at least 96%, at least 97%, at least 98%, at least 99% of the molecular weight of bound haemolysis-derived components.

In certain embodiments, the haem-binding molecule is bound to the support in an amount such that under maximal binding of all binding agents bound to the support, haem is 0.5% to 5% of the molecular mass of bound haemolysis-derived components. That is, in such embodiments, if all binding agents on the support had their ligand bound, haem would account for 0.5% to 5% of the total molecular weight of the bound ligands. In certain such embodiments, the haem-binding molecule is bound to the support in an amount such that under maximal binding of all binding agents bound to the support, haem is optionally 0.6% to 4%, 0.7%-3%, 0.8%-2%, 0.9%-1% of the molecular weight of bound haemolysis-derived components.

In certain embodiments, the iron-chelating molecule is bound to the support in an amount such that under maximal binding of all binding agents bound to the support, iron is 0.01% to 2% of the molecular mass of bound haemolysis-derived components. That is, in such embodiments, if all binding agents on the support had their ligand bound, iron would account for 0.01% to 2% of the total molecular weight of the bound ligands. In certain such embodiments, the iron-chelating molecule is bound to the support in an amount such that under maximal binding of all binding agents bound to the support, iron is optionally 0.02% to 1.5%, 0.05%-1%, 0.1%-1%, 0.5%-1% of the total molecular weight of bound haemolysis-derived components.

Each binding agent is bound to the device in an amount effective to reduce the amount of each respective haemolysis-derived component in the blood product for which the device is to be used. It will be appreciated that the necessary amount will depend on the volume of blood in which the device is intended to be used. Naturally this will vary depending on, for example, the size of the blood bag or the flow rate and volume of a flow line. In certain embodiments, the minimum amount of each binding agent bound to the device per millilitre of blood to which the device will be exposed, is an amount sufficient to provide an optimal binding capacity equivalent to:

Haemoglobin-binding molecule: 0.003 micro mols of haptoglobin
Haem-binding molecule: 0.006 micro mols of HSA
Iron-chelating molecule: 0.066 micro mols of DFO.

In certain embodiments, the haemoglobin-binding molecule is present in an amount sufficient to provide an optimal binding capacity equivalent to at least 0.003, at least 0.004, at least 0.005, at least 0.006, at least 0.007, at least 0.008, at least 0.009, at least 0.01, at least 0.015, at least 0.02, at least 0.025 micro mols of haptoglobin.

In certain embodiments, the haem-binding molecule is present in an amount sufficient to provide an optimal binding capacity equivalent to at least 0.006, at least 0.007, at least 0.008, at least 0.009, at least 0.01, at least 0.011, at least 0.012, at least 0.013, at least 0.014, at least 0.015, at least 0.02, at least 0.025 micro mols of HSA.

In certain embodiments, the iron-chelating molecule is present in an amount sufficient to provide an optimal binding capacity equivalent to at least 0.066, at least 0.07, at least 0.075, at least 0.08, at least 0.085, at least 0.09, at least 0.095, at least 0.1, at least 0.11, at least 0.12, at least 0.13, at least 0.14, at least 0.15, at least 0.2 micro mols of DFO.

In certain embodiments, the device reduces haemolysis by at least 40%, optionally at least 50%, at least 60%, at least 70%, at least 80%, at least 85%. Such a percentage decrease in haemolysis is in comparison to an equivalent blood product that has not been exposed to the device.

In certain embodiments, the device reduces the amount of haemoglobin in blood treated with the device by at least 40%, at least 50%, at least 60%, at least 70%, at least 80%, at least 85%, at least 90%, at least 95%, at least 98%, at least 99%. Said percentage decrease in haemoglobin is in comparison to the levels in an equivalent blood product that has not been exposed to the device.

In certain embodiments, the device reduces the amount of haem in blood treated with the device by at least 40%, at least 50%, at least 60%, at least 70%, at least 80%, at least 85%, at least 90%, at least 95%, at least 98%, at least 99%. Said percentage decrease in haem is in comparison to the levels in an equivalent blood product that has not been exposed to the device.

In certain embodiments, the device reduces the amount of iron in blood treated with the device by at least 40%, at least 50%, at least 60%, at least 70%, at least 80%, at least 85%, at least 90%, at least 95%, at least 98%, at least 99%. Said percentage decrease in iron is in comparison to the levels in an equivalent blood product that has not been exposed to the device.

In certain embodiments, the device reduces the amount of haemolysis-derived components in blood treated with the device by at least 40%, at least 50%, at least 60%, at least 70%, at least 80%, at least 85%, at least 90%, at least 95%, at least 98%, at least 99%. Said percentage decrease in haemolysis-derived components is in comparison to the levels in an equivalent blood product that has not been exposed to the device.

A support for use according to the present invention is a substrate to which the binding agents can be bound and immobilised. In certain embodiments of the present invention, the support is in the form of a plurality of beads. Beads according to this embodiment of the invention may be any suitable shape, for example spherical, cylindrical, conical, tubular, cuboid, pyramidal or irregular polygonal shapes. Appropriate beads for use in the invention include those suitable for use in column chromatography and for solid-support organic chemistry, for example beads analogous to those used in affinity chromatography and combinatorial chemistry. In certain embodiments the beads are polysaccharide beads, such as agarose beads. In certain embodiments, the beads are macroporous beads. Other beads suitable for use in the invention would be appreciated by the skilled person.

In certain embodiments wherein the support is a plurality of beads, each bead of the plurality of beads is bound to no more than one of the iron-chelating molecule, the haemoglobin-binding molecule, and the haem-binding molecule. That is, each bead has only one type of binding agent bound to it. For the avoidance of doubt, in such embodiments, each bead may still have multiple binding agent molecules bound to it, but those molecules are of the same type. In such embodiments, the proportions of binding agents described above can be achieved by combining beads, each bound to one type of binding agent, in the required percentages.

In certain embodiments, the beads are agarose beads. In such embodiments, the binding agents may be bound to the beads using the following reaction scheme:

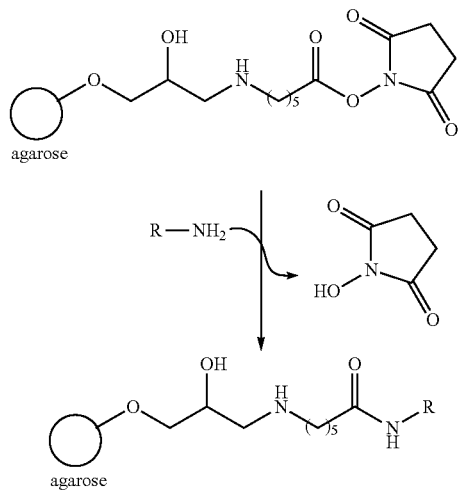

In this reaction scheme, the agarose beads comprise an activated N-hydroxysuccinimidyl ester at the end of a 10-atom spacer. The binding agents are then bound to the beads by means of a substitution reaction between a primary amine on the binding agent and the N-hydroxysuccinimidyl leaving group.

In certain embodiments of the invention, the plurality of beads may be provided loose, i.e. not contained. Alternatively, in certain embodiments the plurality of beads may be contained. In certain such embodiments, the beads may be provided in a "teabag" structure. As will be appreciated by the skilled person, a "teabag" is a structure able to be suspended in a liquid, the structure being made up of a membrane able to contain the beads and which is sufficiently porous to allow the liquid to move through the membrane (in both directions) and thereby allowing the liquid to circulate around the beads. Preferably the teabag structure is suitable for use in blood.

In certain embodiments of the present invention, the support is formed as a single element. That is, in such embodiments, all binding agents are bound to one single continuous support. Examples of supports formed as single elements include: a laminate layer to which all binding agents are bound or a three-dimensional solid the surface or surfaces of which are coated with the binding agents. Such a solid may be in the form of a rigid disk or cartridge, a mesh, a capillary matrix or a honeycomb matrix, for example a cross-linked polystyrene matrix.

In certain embodiments the support may be formed of fibres. In certain such embodiments the fibres are formed into a mesh. In certain such embodiments the fibres form a filter, optionally a size-exclusion filter.

In certain embodiments, the device of the present invention further comprises a vessel for the storage or passage of blood, wherein the vessel contains the support. Vessels suitable for the storage or passage of blood include those vessels which are physiologically inert and clinically suitable to contain blood and blood products to be administered to a subject. These include blood bags (for example blood bags used to store donated blood for future transfusion), catheters, cannulae, a portion of a flow line (a flow line being apparatus used for delivery of fluids to a subject, for example intravenously or intra-arterially), syringes, and the components of extracorporeal circuits (for example those used for cardiopulmonary bypass or haemodialysis, and cardiac pumps). The skilled person will appreciate that such vessels can be used in combination: for example, blood that has passed through an extracorporeal circuit can pass through a flow line and into a subject via a cannula, any one or more of which may include a device according to the present invention.

In certain preferred embodiments, the vessel is a blood bag. In certain such embodiments, the blood bag is for the storage of blood to be used in future transfusions. In certain preferred embodiments, the vessel is a flow line for delivery of blood to a patient, for example from a blood bag or extracorporeal circuit. In certain such embodiments, the support contained by the flow line may be housed in a flow chamber. A flow chamber according to this embodiment is arranged so as to allow a sufficient volume of the blood to contact the binding agents bound to the support for the haemolysis-derived components to be removed, but to maintain an acceptable flow rate of the blood through the flow chamber and into the patient. In one such embodiment the flow chamber is a bead column provided in the flow line, with a lumen diameter and bead density sufficient to allow an acceptable blood flow rate, for example a flow rate of 100-500 ml/min, for example a flow rate of 200 ml/min.

In certain embodiments of the invention wherein the device comprises a vessel for the storage or passage of blood which contains the support, the support may be partially or wholly integrated with the vessel. In certain embodiments wherein the support is partially integrated with the vessel, the support may be anchored to the vessel from a site on the support. For example, in embodiments wherein the support is a single element or teabag of beads, the support may be anchored or tethered to the vessel at one or more positions on the support, but is otherwise able to move freely. Such an arrangement would have the additional advantage that, in use, the support is able to circulate within the blood or flow of blood, but will not be at risk of blocking the flow of blood, as may happen if the support was to float freely.

In certain other embodiments, the support is wholly integrated with the vessel. In such embodiments, the support may form the inner luminal surface of the vessel, for example the support may be the inner surface of the blood bag, or inner surface of the flow line. In other such embodiments, the support may be housed in, and form the structure of, a flow chamber. For example, the inner structure of the flow chamber may be the support in the form of a capillary matrix or honeycomb matrix.

In certain alternative embodiments, the support is not integrated with the vessel. In such embodiments the support is not fixed to the inner luminal surface of the vessel. For example, in embodiments wherein the support is a plurality of beads and the vessel is a flow line, the beads may be loose but contained in a flow chamber. In embodiments wherein the support is a plurality of beads and the vessel is a blood bag, the plurality of beads may be provided as a teabag of beads that is not anchored to the vessel.

In certain embodiments according to the present invention, the support is manufactured from an insoluble polymer or glass. Suitable insoluble polymers or glasses are those which are clinically approved for contact with blood products to be administered to a patient and to which the binding agents can be bound. Such suitable insoluble polymers include natural functionalised biopolymers, such as a polysaccharide polymer (e.g. agarose), and synthetic polymers, such as polystyrene-, polyacrylamide-, and polyethylene-based polymers. In certain embodiments, the synthetic polymer is a co-polymer/grafted, e.g. PEGylated. In certain embodiments the insoluble polymer is agarose.

In a further aspect of the present invention is provided an apparatus comprising a device according to the first aspect of the invention. In certain embodiments, the apparatus is for extracorporeal blood circulation, such as in cardiopulmonary bypass, haemodialysis, extracorporeal membrane oxygenation, or is for in situ use, for example as part of a ventricular assist device.

In a further aspect of the present invention, a method of removing haemolysis-derived components from blood is provided, the method comprising applying the blood to a device or apparatus according to the invention. In certain embodiments, the method is applied to blood prior to or at the time of transfusion of the blood into a patient, for example to stored blood from a blood bag. In certain embodiments, the method is applied to blood that has been extracted from a subject into an extracorporeal circuit, before the blood with haemolysis-derived components removed is reintroduced into the patient.

A method of reducing haemolysis in blood is provided, the method comprising applying the blood to a device or apparatus according to the invention. In certain embodiments, the method is applied to blood prior to or at the time of transfusion of the blood into a patient, for example to stored blood from a blood bag. In certain embodiments, the method is applied to blood that has been extracted from a subject into an extracorporeal circuit, before the blood with haemolysis-derived components removed is reintroduced into the patient.

The removal of haemolysis-derived components and reduction in haemolysis when using the method of the invention is particularly effective as the combination of binding agents provides a "single-action" filter. Such a "single action" device allows all types of haemolysis-derived components to be removed in a single step, thereby reducing the demonstrated risk of haemolysis triggered by exposure to filter substrates being exacerbated during sequential filter steps.

In a further aspect of the present invention, a method of treating or preventing a haemolysis-associated pathology in a subject is provided, the method comprising applying blood from a subject to a device or an apparatus according to the present invention and administering said blood to a subject. In certain preferred embodiments, the subject from which the blood is taken and the subject to which the blood is administered is the same subject. According to this method, the blood administered to the subject has had haemolysis-derived components removed. The method therefore prevents the haemolysis-associated pathologies that may be caused by administration or transfusion of blood containing haemolysis-derived components, for example as a result of storage, mechanical, osmotic or thermal stresses. The method also treats haemolysis-associated pathology as the administered blood has low levels of haemolysis-derived components and therefore dilutes the levels of these haemolysis-derived components circulating in the subject. Moreover, in embodiments in which the blood to which the method is applied is from the same patient to which it is administered according to the method, then the method acts to remove haemolysis-derived components causing haemolysis-associated pathology that are circulating in the subject in a dialysis-type treatment.

Haemolysis-associated pathologies suitable to be prevented and treated by methods according to this aspect of the invention include hypertension, vaso-occlusion, vascular injury, atherosclerosis, organ injury (for example renal failure, liver damage, renal tubular injury, extramedullary haematopoiesis, and acute lung injury), acute respiratory distress syndrome, and systemic inflammatory response syndrome.

Haemolysis-associated pathologies may be caused by the following, each of which may be treated by methods according to the invention: haemolytic anaemia, haemoglobinopathy (e.g. sickle cell disease, thalassemia (alpha, beta or delta)), autoimmune-induced haemolysis (e.g. Paroxysmal nocturnal haemoglobinuria (PNH)), drug-induced autoimmune haemolysis, drug-induced non-autoimmune haemolysis, infection (e.g. malaria, yellow fever, dengue fever), haemorrhagic conditions, HELLP syndrome. Haemolysis-associated pathologies may also be caused by administration of stored blood, administration of shed blood, or use of a cardiac pump, whether extracorporeal (e.g. as part of dialysis or extracorporeal membrane oxygenation (ECMO)) or in situ (e.g. a ventricular assist device). Use of methods, devices or apparatuses according to the invention can treat or prevent haemolysis-associated pathologies caused by these conditions by removing the haemolysis-derived components from blood either before a blood transfusion is administered to a subject, or as part of an extracorporeal circuit to remove haemolysis-derived components that are present in the subject's circulating blood.

In a further aspect of the invention is provided an iron-chelating molecule for use in the treatment or prevention of haemolysis-associated pathology in a subject, wherein the iron-chelating molecule is bound to a support to which at least one haemoglobin-binding molecule, and at least one haem-binding molecule are also bound.

In certain embodiments of this aspect of the invention, the haemolysis-associated pathology treated or prevented is selected from hypertension, vaso-occlusion, vascular injury, atherosclerosis, organ injury, acute respiratory distress syndrome, and systemic inflammatory response syndrome.

In certain embodiments of this aspect of the invention, the haemolysis associated pathology is caused by haemolytic anaemia, a haemoglobinopathy, autoimmune-induced haemolysis (e.g. Paroxysmal nocturnal haemoglobinuria (PNH)), drug-induced autoimmune haemolysis, drug-induced non-autoimmune haemolysis, infection, a haemorrhagic condition, administration of stored blood, administration of shed blood, or use of a cardiac pump, whether extracorporeal (e.g. as part of dialysis or extracorporeal membrane oxygenation (ECMO)) or in situ (e.g. a ventricular assist device).

In a further aspect of the invention is provided a haemoglobin-binding molecule for use in the treatment or prevention of haemolysis-associated pathology in a subject, wherein the haemoglobin-binding molecule is bound to a support to which at least one iron-chelating molecule, and at least one haem-binding molecule are also bound.

In certain embodiments of this aspect of the invention, the haemolysis-associated pathology treated or prevented is selected from hypertension, vaso-occlusion, vascular injury, atherosclerosis, organ injury, acute respiratory distress syndrome, and systemic inflammatory response syndrome.

In certain embodiments of this aspect of the invention, the haemolysis associated pathology is caused by haemolytic anaemia, a haemoglobinopathy, autoimmune-induced haemolysis (e.g. Paroxysmal nocturnal haemoglobinuria (PNH)), drug-induced autoimmune haemolysis, drug-induced non-autoimmune haemolysis, infection, and haemorrhagic condition, administration of stored blood, administration of shed blood, or use of a cardiac pump, whether extracorporeal (e.g. as part of dialysis or extracorporeal membrane oxygenation (ECMO)) or in situ (e.g. a ventricular assist device).

In a further aspect of the invention is provided a haem-binding molecule for use in the treatment or prevention of haemolysis-associated pathology in a subject, wherein the haem-binding molecule is bound to a support to which at least one haemoglobin-binding molecule, and at least one iron-chelating molecule are also bound.

In certain embodiments of this aspect of the invention, the haemolysis-associated pathology treated or prevented is selected from hypertension, vaso-occlusion, vascular injury, atherosclerosis, organ injury, acute respiratory distress syndrome, and systemic inflammatory response syndrome.

In certain embodiments of this aspect of the invention, the haemolysis associated pathology is caused by haemolytic anaemia, a haemoglobinopathy, autoimmune-induced haemolysis (e.g. Paroxysmal nocturnal haemoglobinuria (PNH)), drug-induced autoimmune haemolysis, drug-induced non-autoimmune haemolysis, infection, a haemorrhagic condition, administration of stored blood, administration of shed blood, or use of a cardiac pump, whether extracorporeal (e.g. as part of dialysis or extracorporeal membrane oxygenation (ECMO)) or in situ (e.g. a ventricular assist device).

In all relevant aspects and embodiments of the present invention, the subject or subjects is preferably a mammalian subject, more preferably a human subject.

Unless stated to the contrary or clearly incompatible, any of the embodiments of the invention may be used in combination with any one or more of the other embodiments of the invention.

EXAMPLES

Example 1

Immobilisation of Binding Agents

A haemoglobin (Hb)-binding molecule (haptoglobin), a haem-binding molecule (human serum albumin (HSA)), and an iron-chelating molecule (desferrioxamine (DFO)) were bound to agarose beads in three separate batches, such that any one bead is bound only to one of haptoglobin, HSA and DFO. Each binding agent was bound to the beads using the following reaction scheme:

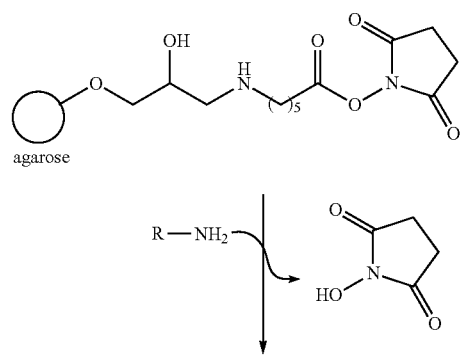

-continued

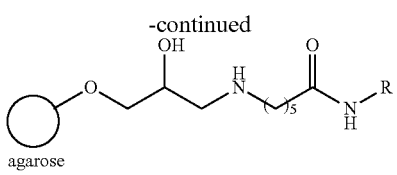

In this reaction scheme, the agarose beads comprise an activated N-hydroxysuccinimidil ester at the end of a 10-atom spacer. The binding agents are then immobilised on the beads by means of a substitution reaction between a primary amine on the binding agent and the N-hydroxysuccinimidil leaving group.

Maximal loading of each bead each binding agent was determined to be: HSA—22.23 mg of HSA/ml of beads; DFO—24.2 mg of DFO/ml of beads; haptoglobin (Hp)—10.3 mg of Hp/ml of beads.

The respective functionalised beads were demonstrated to pull each of the haemolysis-derived components (haemoglobin, haem and free iron) out of solution. Using beads loaded with 2.7 HSA mg/mL bead, and a haem stock of 18.6 µg/mL, a total of 1.3±0.2 µg/mL of bead was bound after 2 hours (50% binding). Similarly, DFO loaded agarose beads could bind and remove free ferric ions out of solution. Using a stock of either $Fe^{2+}$ (3.4 µg/mL) or $Fe^{3+}$ (3.7 µg/mL), binding to DFO (22.3 mg/mL bead loading) was observed (2.59 mg/mL bead, 3.05 mg/mL bead respectively).

For haptoglobin (Hp), maximal haemoglobin (Hb) binding capacity was determined (FIG. 3).

Example 2

Time Course of Stored RBCs

Materials and Methods
Isolation and Storage

Whole blood (450 mL±10%) was collected from a single healthy volunteer into a blood bag (Fernesus) containing CPDA-1 anticoagulant (63 mL). After separation of plasma by centrifugation (10 min, 2000×g), the sample was leukodepleted, after which plasma was reintroduced (17% of total volume). At this stage, the RBCs were divided into individual wells (4.1 mL in each, vide infra), to which 2.9 mL of an additive solution (either 10 mM isotonic citrate-phosphate buffer, or AS-3—both pH 5.8) were added to make a final volume of 7 mL. Functionalised beads (beads to which haptoglobin, HSA and DFO had been bound), and control beads (without any binding agents) were added according to the following scheme in Table 1. Plates were prepared in triplicate. The functionalised beads were a mixture of haptoglobin-, HSA- and DFO-functionalised beads in the proportions 80%, 15%, and 5% respectively.

The plates were incubated with gentle rocking at room temperature for 7 days, in order to accelerate haemolysis.

TABLE 1

| FP | CP | BP | Citrate-phosphate buffer |
|---|---|---|---|
| FA | CA | BA | AS-3 buffer |
| Functionalised Beads | Control Beads | Blank (no beads) | |

Extracellular pH was measured daily using a micro-volume electrode (Jenway). Percent haemolysis was determined through the comparison of free haemoglobin in the supernatant (Hbs) versus total haemoglobin (HbT), and correcting for haematocrit (Hct):

% haemolysis=$(Hb_s\times(100-\% Hct))/Hb_T$

Supernatant was prepared using two centrifugation steps. The sample was first subjected to centrifugation at 2000×g for 10 min, after which the supernatant was removed and further spun at 15 000×g for 10 min. The supernatant from the second centrifugations was assayed for $Hb_S$ concentration using the QuantiChrom™ Hemoglobin Assay Kit (BioAssay Systems).

Total haemoglobin was determined by diluting 10 uL of sample in 990 uL MilliQ water, and incubating for an hour as to cause complete haemolysis. The resulting solution was spun at 15 000×g for 10 min and the supernatant assayed for $Hb_T$ concentration using the QuantiChrom™ Hemoglobin Assay Kit (BioAssay Systems). For samples containing beads, the sample was first filtered to remove the beads using a 40 um mesh cell strainer with the aid of gentle centrifugation (500 g, 1 min).

Haematocrit was determined manually by collecting (filtered) sample in microcapillary tubes and spinning in a conventional centrifuge (3500 g for 10 min) by placing a foam insert into a centrifuge tube. The sample Hct was then measured by visually quantifying the percentage of packed cells using a micro-capillary reader.

Results

A considerable decrease in haemolysis was observed for wells containing functionalised beads in comparison to the control wells (blank beads and no beads) (FIG. 4). This effect was observed for both buffers used, and was observed at all time points measured (FIGS. 4 A and B).

The reduction in haemolysis when using the beads functionalised with the 3 binding agents was all the more noteworthy given that exposure to beads alone (control beads) can cause haemolysis rates to increase (FIG. 4—Control Beads vs Blank). This demonstrates that the use of beads functionalised with a haemoglobin (Hb)-binding molecule, a haem-binding molecule and an iron-chelating molecule is able to greatly reduce haemolysis and, further, overcome the increased haemolysis observed when RBCs are exposed to filter substrates.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The invention claimed is:

1. A device for removal of haemolysis-derived components from blood, the device comprising:
   a support, and
   a plurality of binding agents bound to said support,
   wherein the binding agents comprise at least one iron-chelating molecule, at least one haemoglobin-binding molecule, and at least one haem-binding molecule,
   wherein the haemoglobin-binding molecule, the haem-binding molecule, and the iron-chelating molecule are present in the respective proportions 50-90%, 5-50% and 1-30% of the binding agents bound to the support, such that the sum of the proportions equals 100% of the binding agents bound to the support, and
   whereby the at least one iron-chelating molecule, the at least one haemoglobin-binding molecule, and the at least one haem-binding molecule are able to bind and to remove out of solution haemolysis-derived iron, haemoglobin, and haem, respectively, from blood contacted with the device, wherein the haemolysis from which the iron, haemoglobin and haem are derived occurred in the blood contacted with the device.

2. A device according to claim 1 further comprising a vessel for the storage or passage of blood, wherein the vessel contains the support.

3. A device according to claim 2, wherein the support is wholly or partially integrated with the vessel.

4. A device according to claim 2, wherein the support is not integrated with the vessel.

5. A device according to claim 1, wherein the support is a plurality of beads.

6. A device according to claim 5, wherein each bead of the plurality of beads is bound to no more than one of: the iron-chelating molecule, the haemoglobin-binding molecule, and the haem-binding molecule.

7. A device according to claim 1, wherein the support is a single element to which at least one iron-chelating molecule, at least one haemoglobin-binding molecule, and at least one haem-binding molecule are bound.

8. A device according to claim 1, wherein the support comprises an insoluble polymer or a glass.

9. A device according to claim 1, wherein the iron-chelating molecule is desferrioxamine, the haemoglobin-binding molecule is haptoglobin, and the haem-binding molecule is serum albumin.

10. A device according to claim 1, wherein the device is for in vitro or ex vivo removal of haemolysis-derived components from blood.

11. A device according to claim 1 wherein the device is a component of an extracorporeal blood circulation apparatus or an apparatus comprising a flow line for delivering blood from a blood bag to a patient.

12. A method for removing haemolysis-derived components from a blood sample, the method comprising applying the blood sample to a device according to claim 1, wherein the at least one iron-chelating molecule, the at least one haemoglobin-binding molecule, and the at least one haem-binding molecule remove haemolysis-derived iron, haemoglobin and haem, respectively, from the blood sample applied to the device.

13. A method according to claim 12 wherein the device is a component of an extracorporeal blood circulation apparatus or an apparatus comprising a flow line for delivering blood from a blood bag to a patient.

14. A method of treating or preventing haemolysis-associated pathology in a subject, the method comprising applying blood from a subject to a device according to claim 1 such that the at least one iron-chelating molecule, the at least one haemoglobin-binding molecule, and the at least one haem-binding molecule bind and remove out of solution haemolysis-derived iron, haemoglobin and haem, respectively, from the blood applied to the device, and administering said blood to a subject, such that haemolysis-associated pathology as a result of the blood being administered is reduced.

15. A method according to claim 14 wherein the device is a component of an extracorporeal blood circulation apparatus or an apparatus comprising a flow line for delivering blood from a blood bag to a patient.

16. A device according to claim 1, wherein the support is a single element to which the at least one iron-chelating molecule, the at least one haemoglobin-binding molecule, and the at least one haem-binding molecule are bound, wherein all of the plurality of binding agents are bound to the single element.

17. A device according to claim 1 wherein the support comprises an insoluble polymer that is agarose or a PEGylated synthetic polymer.

18. A device according to claim 1, further comprising a vessel for the storage or passage of blood, wherein the vessel contains the support;
   wherein the support is a single element to which at least one iron-chelating molecule, at least one haemoglobin-binding molecule, and at least one haem-binding molecule are bound; and
   wherein the support is not integrated with the vessel.

19. A method according to claim 14 wherein the subject from which the blood is taken and the subject to which the blood is administered is the same subject.

* * * * *